US007632525B2

(12) United States Patent
Dodds et al.

(10) Patent No.: US 7,632,525 B2
(45) Date of Patent: *Dec. 15, 2009

(54) BREATH FRESHENING AND ORAL CLEANSING PRODUCT WITH MAGNOLIA BARK EXTRACT IN COMBINATION WITH SURFACE ACTIVE AGENTS

(75) Inventors: Michael William James Dodds, Chicago, IL (US); James Roy Maxwell, Chicago, IL (US); Michael J. Greenberg, Northbrook, IL (US); Minmin Tian, Naperville, IL (US); Rebecca Ann Aumann, Chicago, IL (US)

(73) Assignee: Wm. Wrigley Jr. Company, Chicago, IL (US)

(*) Notice: Subject to any disclaimer, the term of this patent is extended or adjusted under 35 U.S.C. 154(b) by 63 days.

This patent is subject to a terminal disclaimer.

(21) Appl. No.: 11/181,579

(22) Filed: Jul. 14, 2005

(65) Prior Publication Data
US 2006/0013779 A1 Jan. 19, 2006

Related U.S. Application Data

(63) Continuation-in-part of application No. 10/606,671, filed on Jun. 25, 2003.

(60) Provisional application No. 60/319,346, filed on Jun. 25, 2002.

(51) Int. Cl.
*A61K 36/00* (2006.01)
*A61Q 11/00* (2006.01)

(52) U.S. Cl. .......................... 424/725; 424/49; 424/58; 424/56

(58) Field of Classification Search .................. 424/49, 424/58, 56, 725
See application file for complete search history.

(56) References Cited

U.S. PATENT DOCUMENTS

| 1,056,212 | A | | 3/1913 | Puetzer et al. |
|---|---|---|---|---|
| 3,452,138 | A | | 6/1969 | Granatek et al. |
| 4,310,141 | A | * | 1/1982 | Tamura ............ 251/28 |
| 4,547,361 | A | | 10/1985 | Steltenkamp et al. |
| 4,562,020 | A | | 12/1985 | Hijiya et al. |
| 4,568,560 | A | | 2/1986 | Schobel |
| 4,820,544 | A | | 4/1989 | Barcelon et al. |
| 4,971,806 | A | | 11/1990 | Cherukuri et al. |
| 5,120,528 | A | * | 6/1992 | Chang et al. ............ 424/49 |
| 5,149,521 | A | | 9/1992 | Hirose et al. |
| 5,487,902 | A | | 1/1996 | Andersen et al. |
| 5,651,997 | A | | 7/1997 | Makino et al. |
| 5,885,554 | A | * | 3/1999 | Michael et al. ......... 424/49 |
| 5,939,050 | A | | 8/1999 | Iyer et al. |
| 5,948,430 | A | | 9/1999 | Zerbe et al. |
| 6,177,096 | B1 | | 1/2001 | Zerbe et al. |
| 6,248,309 | B1 | | 6/2001 | Iyer et al. |
| 6,280,751 | B1 | | 8/2001 | Fletcher et al. |
| 6,284,264 | B1 | | 9/2001 | Zerbe et al. |
| 6,495,512 | B1 | | 12/2002 | White et al. |
| 6,500,406 | B1 | | 12/2002 | Rajaiah et al. |
| 6,500,409 | B1 | | 12/2002 | Scherl et al. |
| 6,552,024 | B1 | | 4/2003 | Chen et al. |
| 6,582,735 | B2 | | 6/2003 | Stogniew et al. |
| 6,596,298 | B2 | | 7/2003 | Leung et al. |
| 6,656,493 | B2 | | 12/2003 | Dzija et al. |
| 6,703,000 | B2 | | 3/2004 | Ning et al. |
| 6,719,962 | B2 | | 4/2004 | Day et al. |
| 6,723,326 | B1 | | 4/2004 | Farmer |
| 6,726,897 | B2 | | 4/2004 | Lawlor et al. |
| 6,740,332 | B2 | | 5/2004 | Zyck et al. |
| 6,923,981 | B2 | | 8/2005 | Leung et al. |
| 7,025,983 | B2 | | 4/2006 | Leung et al. |
| 2001/0018043 | A1 | | 8/2001 | Henning et al. |
| 2001/0022964 | A1 | | 9/2001 | Leung et al. |
| 2002/0131990 | A1 | | 9/2002 | Barkalow et al. |
| 2003/0007997 | A1 | | 1/2003 | Lawlor |
| 2003/0008062 | A1 | | 1/2003 | Day et al. |
| 2003/0049303 | A1 | | 3/2003 | Ning et al. |
| 2003/0224090 | A1 | | 12/2003 | Pearce et al. |
| 2004/0081713 | A1 | | 4/2004 | Maxwell et al. |
| 2004/0086546 | A1 | | 5/2004 | Maxwell et al. |
| 2004/0253189 | A1 | | 12/2004 | Maxwell et al. |
| 2004/0253190 | A1 | | 12/2004 | Maxwell et al. |

(Continued)

FOREIGN PATENT DOCUMENTS

CN 1094895 11/1994

(Continued)

OTHER PUBLICATIONS

Al/Zuhair et al. *Pharmacological Research*, vol. 34, No. 1/2, 1996.

(Continued)

*Primary Examiner*—Ruth A Davis
(74) *Attorney, Agent, or Firm*—Brinks Hofer Gilson & Lione

(57) ABSTRACT

An oral composition for oral cleansing, breath freshening, and anti-microbial benefits includes Magnolia Bark Extract in combination with a surface active agent. The effectiveness of Magnolia Bark Extract in inhibiting biofilm formation in the oral cavity is increased by a synergistic combination of the Magnolia Bark Extract with a surface active agent in an oral cavity delivery agent, such as chewing gum, a confectionary, a lozenge, a compressed tablet, and an edible film.

16 Claims, No Drawings

U.S. PATENT DOCUMENTS

| | | |
|---|---|---|
| 2004/0253191 A1 | 12/2004 | Maxwell et al. |
| 2004/0253192 A1 | 12/2004 | Maxwell et al. |
| 2004/0253278 A1 | 12/2004 | Maxwell et al. |
| 2004/0258733 A1 | 12/2004 | Maxwell et al. |
| 2005/0008690 A1 | 1/2005 | Miller |
| 2005/0013902 A1 | 1/2005 | Pearce |
| 2005/0031718 A1 | 2/2005 | Zhu et al. |

FOREIGN PATENT DOCUMENTS

| | | |
|---|---|---|
| CN | 1094895 A | 11/1994 |
| CN | 1096694 A | 12/1994 |
| CN | 1096699 A | 12/1994 |
| CN | 1115212 A | 1/1996 |
| CN | 1127136 A | 7/1996 |
| CN | 1141194 A | 1/1997 |
| CN | 1073410 C | 10/2001 |
| GB | 1311060 | 3/1973 |
| JP | 57085319 A | 5/1982 |
| JP | 84-175422 | 10/1984 |
| JP | 1151512 | 6/1989 |
| KR | 1996-0007923 | 6/1996 |
| KR | 2002-0003413 | 1/2002 |
| WO | WO 93/15116 | 8/1993 |
| WO | WO 97/35599 | 10/1997 |
| WO | WO 99/18940 | 4/1999 |
| WO | WO 99/51093 | 10/1999 |
| WO | WO 00/42992 A2 | 7/2000 |
| WO | WO 01/82922 A1 | 11/2001 |
| WO | WO 01/85116 * | 11/2001 |
| WO | WO 02/43657 A2 | 6/2002 |
| WO | WO 02/091848 A1 | 11/2002 |
| WO | WO 2004/000235 | 12/2003 |
| WO | WO 2007/011504 | 1/2007 |
| WO | WO 2007/064505 | 6/2007 |

OTHER PUBLICATIONS

Bang K.H. et al., *Archives of Pharmaceutical Research*, vol. 23, pp. 46-49, 2000.
Chang B. et al., *Planta Medica*, vol. 64, pp. 367-369, 1998.
Ho, K at al., *Phytotherapy Research*, vol. 15, pp. 139-141, 2001.
Kubo I. et al., *J. Agric. Food Chem.*, vol. 41, pp. 2447-2450, 1993.
Mori M. et al., *Holz als Roh-und Werkstoff*, vol. 55, pp. 275-278, 1997.
Park, J. et al., *European Journal of Pharmacology*, vol. 496, pp. 189-195, 2004.
Rickard A.H. et al., *Trends in Microbiology*, vol. 11, pp. 94-100, 2003.
Schreiner H.C. et al., *PNAS*, vol. 100, pp. 7295-7300, 2003.
Sharma A. et al., *Oral Microbiology and Immunology*, vol. 20, pp. 39-42, 2005.
Watanabe K. et al. *Japanese Journal of Pharmacology*, vol. 25, pp. 605-607, 1975.
PCT International Search Report, PCT/US2006/025042, Sep. 10, 2006.
PCT Written Opinion, PCT/US2006/025042, Sep. 10, 2006.
PCT International Search Report, PCT/US2007/006989, Dec. 19, 2007.
PCT Written Opinion, PCT/US2007/006989, Dec. 19, 2007.
International Search Report, PCT/US2006/044934, Mar. 14, 2007.
PCT International Search Report, PCT/US2006/044810, Mar. 7, 2007.
PCT Written Opinion, PCT/US2006/044810, Mar. 7, 2007.
PCT International Search Report, PCT/US2006/044933, Mar. 8, 2007.
PCT Written Opinion, PCT/US2006/044933, Mar. 8, 2007.

* cited by examiner

BREATH FRESHENING AND ORAL CLEANSING PRODUCT WITH MAGNOLIA BARK EXTRACT IN COMBINATION WITH SURFACE ACTIVE AGENTS

RELATED U.S. APPLICATION

This application is a continuation-in-part of U.S. patent application Ser. No. 10/606,671, filed Jun. 25, 2003, which claims priority to provisional patent application Ser. No. 60/319,346, filed Jun. 25, 2002.

TECHNICAL FIELD

The present invention relates, in general, to confectionary compositions and, more particularly, to confectionary compositions containing Magnolia Bark Extract and to methods of making the confectionary compositions.

BACKGROUND

There is considerable consumer demand for products that freshen breath and kill bacteria in the mouth. An oral product with breath freshening and bactericidal benefits is a convenient delivery for oral cleansing in the oral cavity and freshening breath. Bacteria in the oral cavity, particularly on the tongue, can generate volatile sulfur compounds, which are a major cause of bad breath. Of course, breath freshening is a very important part of everyday life.

In order to facilitate proper oral hygiene, oral cleansing and breath freshening practices should be conducted repeatedly throughout the day. However, oral cleansing and breath freshening may be difficult or inconvenient at times, depending on the nature of the breath freshening desired and the situation in which the breath freshening must occur. Brushing, flossing, cleaning your tongue and gargling using a variety of devices and compositions are common oral care practices well-suited for the privacy of one's home. But, such devices and compositions are less convenient to use away from the home where bathroom facilities might be scarce, unavailable or unsanitary.

Dental plaque is a microbial deposit that forms on teeth within a short time of brushing. It has been described by researchers as a soft, concentrated mass consisting mainly of a large variety of bacteria together with a certain amount of cellular debris which develops within a short time of refraining from toothbrushing. Dental plaque is not removed by rinsing with water. More recently researchers have recognized that plaque is a microbial biofilm. Dental plaque has been described as a diverse community of micro-organisms found on the tooth surface as a biofilm. The biofilm is embedded in an extracellular matrix of polymers that originate from both the tooth surface and the microbial organisms. It is generally recognized that a reduction in dental plaque promotes clean teeth, fresh breath, and healthy gums. The dental plaque biofilm, however, is very resistant to antimicrobial agents.

Antimicrobials agents that have been shown to have definite plaque-reducing abilities include chlorhexidine, cetylpyridinium chloride (CPC), Triclosan and Delmopinol. These are all medicinal and non-natural agents. Essential oils such as thymol, Eucalyptol, methyl salicylate, and menthol along with other essential oils in an alcohol-based vehicle have also been found to reduce plaque. While thymol is most effective in reducing plaque, it has a disagreeable taste. Generally, these oils benefit from the presence of an alcohol to facilitate their solubility and penetration of the plaque biofilm. While suitable for oral treatments, such as mouthwashes, high concentrations of alcohols can leave a bitter aftertaste in oral compositions, such as gums, edible films, and confectionaries, and the like.

An active ingredient, or a combination of active ingredients, that can provide the benefits of either removing plaque, preventing or slowing down plaque formation, or that has an anti-inflammatory effect that would help maintain the healthy state of the gums would promote health gums and fresh breath. It is known to incorporate active agents into oral compositions for the purpose of providing oral benefits including breath freshening and bactericidal properties. Such systems have the advantage of providing rapid, efficient, and convenient delivery.

BRIEF SUMMARY

In accordance with the present invention it has been unexpectedly discovered that Magnolia Bark Extract in combination with certain surface active agents is synergistically effective in inhibiting the growth of plaque-causing bacteria. The combination of Magnolia Bark Extract and selected surface active agent shows enhanced antiplaque growth activity in excess of either Magnolia Bark Extract or the surface active agent alone.

The present invention further relates to oral compositions containing Magnolia Bark Extract in combination with a surface active agent intended for bactericidal and breath freshening properties. More specifically, the present invention relates to an oral cavity delivery agent, such as a dentifrice, chewing gum, confection, lozenge, mouth spray or edible film containing an effective amount of Magnolia Bark Extract in combination with a surface active agent, by which the inventive composition effectively inactivates or kills oral bacteria and freshens breath through the consumption of the dentifrice, chewing gum, confection, lozenge, mouth spray or edible film product. The surface active agent is added to the oral composition to synergistically increase the effectiveness of the Magnolia Bark extract.

In one aspect of the invention an oral composition for freshening the breath of consumers of the oral composition includes an oral cavity delivery agent and an effective amount of an antimicrobial agent comprising a synergistic ratio of Magnolia Bark Extract and surface active agents, wherein the synergistic ratio is at least about 1 part Magnolia Bark Extract to 1 part surface active agent.

Suitable surface active agents include, but are not limited to, common surfactants, soaps, wetting agents, and emulsifiers. Some examples of surfactants include, but are not limited to, salts of potassium, ammonium, or sodium. Sodium salts include anionic surfactants, such as alkyl sulfates, including sodium lauryl sulfate, sodium laureth sulfate, and the like. Other sodium salts include sodium lauroyl sarcosinate, sodium brasslate, and the like. Suitable ammonium salts include ammonium lauryl sulfate, ammonium laureth sulfate, ammonium lauroyl sarcosinate, ammonium brasslate, ammonium cocamidopropyl betaine, and the like. Other suitable surface active agents include emulsifiers, which can be fatty acids (for example, stearic, palmitic, oleic, and linoleic acids), their salts, glycerol monostearate, glycerol triacetate, lecithin, mono and triglycerides, and acetylated monoglycerides. As will be described below, several suitable surface active agents also show some bactericidal (germ-kill) properties on their own.

In another aspect of the invention, the oral product is chewing gum or any variation including but not limited to bubble gums, pellets, gum balls or sticks. Chewing gums may be coated or not coated and be of a variety of flavors, shapes and sizes. A chewing gum composition for freshening the breath of consumers includes a water soluble bulk portion, at least one flavoring agent, a gum base portion, and an effective amount of an antimicrobial agent comprising a synergistic ratio of Magnolia Bark Extract and surface active agent, wherein the synergistic ratio is at least about 1 part Magnolia Bark Extract to 1 part surface active agents.

In yet another aspect of the invention, the oral product is a confectionery composition including but not limited to hard candy, chewing candy, filled candy and pressed tablets. A confectionary composition for freshening the breath of consumers includes at least one of a sugar or a sugar alcohol and an effective amount of an antimicrobial agent comprising a synergistic ratio of Magnolia Bark Extract and surface active agent, wherein the synergistic ratio is at least about 1 part Magnolia Bark Extract to 1 part surface active agent.

In still another aspect of the invention, the oral product is an edible film composition that includes an effective amount of a film forming agent, and an effective amount of an antimicrobial agent comprising a synergistic ratio of Magnolia Bark Extract and surface active agent, wherein the synergistic ratio is at least about 1 part Magnolia Bark Extract to 1 part surface active agent.

In a further aspect of the invention, a method of oral cleansing includes applying an oral composition to the oral cavity, where the oral composition includes an effective amount of an antimicrobial agent where the antimicrobial agent comprises a synergistic ratio of Magnolia Bark Extract and surface active agent, wherein the synergistic ratio is at least about 1 part Magnolia Bark Extract to 1 part surface active agent.

DETAILED DESCRIPTION

It is known to use chewing gum, confections and thin films as a vehicle for delivering components to the oral cavity which provide oral benefits such as breath freshening and bactericidal properties. Such systems have the advantage of providing a consumer with a convenient and inexpensive method for maintaining oral health and fresh breath throughout the course of the day.

The present invention incorporates Magnolia Bark Extract as the active component for breath freshening and oral bactericidal benefits. Magnolia Bark Extract is known to have bactericidal and antifungal properties. Magnolol and honokiol are two components in Magnolia Bark Extract with antimicrobial activity.

The Magnolia Bark Extract used in the present invention may be obtained from O'Laughlin Industries Co., LTD, Guang Zhou Masson Pharmaceutical Co., or Honsea Sunshine Bioscience and Technology Co. The Magnolia Bark Extract is obtained in the form of a powder. The Magnolia Bark Extract is dissolved with the flavor and may be warmed to dissolve prior to making the oral product.

While it is relatively easy to kill bacteria in solutions, the plaque biofilm is a complex environment that provides protection from environmental threat to the bacteria, as well as synergies between bacterial species (A. Sharma, S. Inagaki, W. Sigurdson, H. K. Kuramitsu, 2005, Synergy between *Tannerella forsythia* and *Fusobacterium nucleatum* in biofilm formation, *Oral Microbiology and Immunology*, 20: 39-42). Therefore, compared to a simple germ kill test, it is much harder to show actual efficacy against established plaque by an anti-microbial agent. Diffusion into the biofilm is limited, and bacteria within the bulk of the biofilm are protected from exposure to the agent by extracellular material, such as the glucan and dextran polysaccharides. It is, therefore, arguably easier to prevent formation of plaque than it is to remove an established plaque.

In accordance with the present invention, the antimicrobial effects of Magnolia Bark Extract are enhanced through the combination of Magnolia Bark Extract with a surface active agent. Although not intending that the invention be limited to any particular theory, it is believed that the combination of a surface active agent with an effective amount Magnolia Bark Extract can provide an oral composition that promotes the reduction of biofilms in dental plaques and in other areas of the oral cavity, such as the tongue. It is believed that the combination of Magnolia Bark Extract and a suitable surface active agent may prevent bacterial attachment to the acquired pellicle. Such an oral composition can slow down or prevent plaque accumulation. Further, the oral composition of the invention can be effective in the removal of existing plaque in combination with enzymes, additional surface active agents, abrasives or combinations thereof.

A preferred surface active agent is one that increases the solubility of Magnolia Bark Extract and that can be used as a food additive. Suitable surface active agents include but are not limited to common surfactants, soaps, wetting agents, and emulsifiers. Some examples of surfactants include but are not limited to salts of potassium, ammonium, or sodium. Sodium salts include anionic surfactants, such as such as alkyl sulfates, including sodium lauryl sulfate, sodium laureth sulfate, and the like. Other sodium salts include sodium lauroyl sarcosinate, sodium brasslate, and the like. Suitable ammonium salts include ammonium lauryl sulfate, ammonium laureth sulfate, ammonium lauroyl sarcosinate, ammonium brasslate, ammonium cocamidopropyl betaine, and the like. Other suitable surface active agents include emulsifiers, which can be fatty acids (for example, stearic, palmitic, oleic, and linoleic acids), their salts, glycerol monostearate, glycerol triacetate, lecithin, mono and triglycerides, and acetylated monoglycerides. As will be described below, several suitable surface active agents also show some bactericidal (germ-kill) properties on their own.

The oral composition can also include additional breath freshening or oral health ingredients, which can be anti-microbial ingredients. Further, the additional breath freshening or oral health ingredients can comprise food acceptable salts of zinc or copper, cooling agents, pyrophosphates or polyphosphates, and the like.

The invention also includes a treatment method for reducing the number or activity of bacteria in the oral cavity of a consumer comprising the steps of providing an oral composition comprising Magnolia Bark Extract in an amount sufficient to kill or deactivate oral bacteria in combination with a surface active agent and causing a person in need of the treatment to consume the oral composition whereby the bacteria in the oral cavity of the person is reduced or inactivated by the treatment.

In one form, the oral composition is formulated with an oral cavity delivery agent to deliver at least about 0.001% to about 2.0% concentration of Magnolia Bark Extract to the oral cavity. In another form, the oral composition is formulated with an oral cavity delivery agent to deliver at least about 0.01% concentration of Magnolia Bark Extract to the oral cavity. One or more surface active agents are added to the oral composition so as to enhance the effectiveness of the oral composition in the delivery of an effective amount to the oral cavity.

In accordance with one embodiment of the invention, one or more surface active agents are present in the oral composition in a concentration range of about 0.001% to about 2.0%. In the oral composition, Magnolia Bark Extract is combined with a surface active agent in a synergistic ratio that provides enhanced germ-kill effectiveness. The synergistic ratio ranges from about 1 part Magnolia Bark Extract to 1 part surface active agent up to about 4 parts Magnolia Bark Extract to 1 part surface active agent. One particularly effective surface active agent is sodium lauryl sulfate and a particularly effective synergistic composition is about 2 parts Magnolia Bark Extract to 1 part sodium lauryl sulfate.

Given that Magnolia Bark Extract is a hydrophobic compound, there are several oral cavity delivery agents that may be used to enhance the release of the Magnolia Bark Extract from the oral composition. In a chewing gum product, the gum base is hydrophobic, which also inhibits the release of the Magnolia Bark Extract. In the various embodiments of the inventive confectionary composition, the Magnolia Bark Extract is combined with a surface active agent and may be encapsulated, spray dried, or formulated into a coating, or combinations thereof in order to facilitate release of the Magnolia Bark Extract into the oral cavity.

To evaluate the effectiveness of Magnolia Bark Extract, in vitro tests were conducted with three subgingival plaque bacteria associated with oral malodor. The Minimum-Inhibitory-Concentrations (MIC) study protocol is as follows. Chlorhexidine was used as a positive control and sterile water was used as a negative control. Menthol and Tween 80 was used as a solvent for Magnolia Bark Extract. Tween 80 is the common name for Polysorbate 80. Nintysix-well microtiter plates were used for this study. Each well contained $5 \times 10^5$ colony forming units/ml of bacteria, serially diluted agents and bacterial growth medium. All bacterial cultures were incubated at 37° C. and stationary. Bacterial growth was estimated spectrophotometrically at 660 nm, after 48 hours. The MIC for each test bacteria was defined as the minimum concentration of test compound limiting turbidity to less than 0.05 absorbance at 660 nm.

The Minimum-Bactericidal-Concentrations (MBC) were determined using the 96-well microtiter plate serial dilutions as described above for MIC studies. Serial dilutions of cultures in wells showing no visible growth were performed and 10 microliters of culture were plated in triplicate on blood agar plates. Viable colonies were scored after incubation of the plates for 48 hours at 37° C. For each test bacterium, the number of colony forming units/ml (CFU/ml) was determined in the initial inoculum. The MBC was defined as the lowest concentration of a test compound that killed at least 99.9% of the cells present in the initial inoculum.

The results of the studies performed to obtain MIC and MBC of Magnolia Bark Extract (MBE) are as follows. Against *Streptococcus mutans* a Magnolia Bark Extract of 90% had an MIC of 15.62 µg/ml. For *Porphyromonas gingivalis*, the 90% Magnolia Bark Extract had an MIC of 3.91 µg/ml, and the 65% Magnolia Bark Extract had an MIC of 7.82 µg/ml. For *Fusobacterium nucleatum* the 90% Magnolia Bark Extract had an MIC of 3.91 µg/ml and an MBC of 7.82 µg/ml. Against the same organism, the 65% Magnolia Bark Extract had an MIC and MBC of 7.82 µg/ml. Cholorhexidine was the positive control and produced an MIC and MBC of 1.25 µg/ml for all three bacteria. The solvent consisting of water with 10% methanol and 3.8% Tween 80 had no noticeable growth inhibitory effects on any of the three bacteria in the study.

It is also known that Magnolia Bark Extract is effective against *Actinobacillus actinomyecetemcomitans, Prevotella intermedia, Micrococcus luteus*, and *Bacillus subtilis, Veillonella disper, Capnocytophaga gingivalis*, periodontic microorganisms, and gingival fibroblasts.

Further to the results described above, the effect of Magnolia Bark Extract on biofilm formation and removal was compared with different herbal and natural ingredients. Comparative testing was performed using green tea extract, Oolong tea extract, Licorice, and Magnolia Bark Extract (Masson Pharma Magnolia Bark Extract MBE90). The comparative testing included determining the solubility in water, ethanol, water:ethanol mixtures and other solvents (for example, Tween in water), MIC for growth of *S. mutans*, MIC for formation of *S. mutans* biofilm in 96 well plates, and the effect on detachment of *S. mutans* biofilm.

The green tea extract was soluble in water; all other substances were found to be soluble in a 2:1 water:ethanol mixture. Magnolia Bark Extract was also soluble in 0.01 µl of 50% Tween 80 in water.

To further evaluate the effect on *S. mutans* biofilm formation, 96-well microtiter plates were used. Each well contained *S. mutans* ($5 \times 10^6$ CFU/ml), was serially diluted with test compounds and growth medium (BHI with 0.5% sucrose). The controls included inoculated growth medium without test compounds. All plates were incubated at 37° C. under aerobic condition with growth estimated spectrophotometrically (660 nm) after 48h using a microtiter plate reader. Then, the supernatant containing unattached cells was removed from each wells by aspiration, the attached biofilm mass was dissolved with 200 µl 1 N NaOH and the optical density was measured at 660 nm using the microtiter plate reader. Chlorhexidine (40 µg/ml) was used as a positive control.

To further evaluate the effect on *S. mutans* biofilm detachment, sterile 96-well microtiter plates were used where each well was inoculated with *S. mutans* ($5 \times 10^6$ CFU/ml), growth medium (brain-heart-infusion broth (BHI) with 0.5% sucrose), and incubated at 37° C. under aerobic condition for biofilm formation. After 48 hours, the non-attached supernatant was aspirated and serially diluted. Test compounds were added to the pre-formed biofilm and incubated at 37° C. under aerobic condition. The controls included solvent without test compounds. After 30 min, the supernatant was aspirated from wells and the biofilm remaining after treatment was dissolved in 200 µl 1N NaOH, and quantitated at 660 nm using the plate reader. A chlorhexidine positive control was used. If detachment of the biofilm by action of the test compounds occurred, the spectrophotometric absorbance or optical density (OD) should show a decrease compared to the non-treated control.

The results of the comparative testing are show below in Table 1. The test results are presented in units of µg/ml for each of the compounds. In Table 1, and in the following Tables, Magnolia Bark Extract is designated as "MBE" and the chlorhexidine positive control is designated as "CHX."

TABLE 1

| Test | Comparative Effect on MIC and Biofilm (µg/ml) | | | | |
| --- | --- | --- | --- | --- | --- |
| | Green tea | Oolong tea | Licorice | MBE | CHX |
| MIC growth | 250 | 1000 | 250 | 7.8 | 2.5 |
| MIC biofilm formation | 250 | 250 | 250 | 7.8 | 2.5 |
| MIC biofilm detachment | >1000 | >1000 | >10000 | >1000 | >10 |

The data shown in Table 1 indicates that none of the compounds tested were more effective than chlorhexidine at removing the established biofilm. The green tea extract, licorice extract and Magnolia Bark Extract may inhibit *S. mutans* biofilm by inhibiting bacterial growth, since MICs are identical for both growth and biofilm formation. Magnolia Bark Extract was most effective at inhibition of both growth and biofilm formation and, within an order of magnitude of the chlorhexidine positive control.

Although useful to show the comparative effect of Magnolia Bark Extract on biofilm formation and MIC growth, the foregoing test procedure may not effectively mimic the in vivo exposure of an oral composition, such as chewing gum to a developing plaque biofilm. In an in vivo situation, the active could be exposed to the plaque for a defined period of time at a set frequency (for example, for 5 minutes, three times a day). Therefore, a series of comparative experiments were conducted to mimic the in vivo use of potential active ingredients. To perform the tests the buffer compositions listed below in Tables 2 and 3 were prepared.

TABLE 2

Saliva buffer composition
(filter sterilize after preparation)

| Compound | mg/L |
| --- | --- |
| Ammonium chloride | 233 |
| Calcium chloride, dihydrate | 210 |
| Magnesium chloride, hexahydrate | 43 |
| Potassium chloride | 1162 |
| $KH_2PO_4$ (monobasic potassium phosphate) | 354 |
| Potassium thiocyanate | 222 |
| Sodium citrate | 13 |
| Sodium bicarbonate | 535 |
| Dibasic sodium phosphate, $Na_2HPO_4$ | 375 |
| Urea | 173 |

TABLE 3

Supplemented Saliva Medium
(filter sterilize after preparation)

| Ingredient | wt. % |
| --- | --- |
| Whole saliva | 25 |
| Saliva buffer | 45 |
| Modified eagle medium (MEM) | 20 |
| Trypticase soy broth | 10 |

A mixed culture system that utilizes the bacteria from freshly-collected stimulated whole saliva was used. Saliva cell pellets were used to inoculate saliva-coated hydroxyapatite (S-HA) discs. The discs were placed in 24-well cell culture plates and incubated for up to 3 days. Biofilms were exposed to actives on days 2 and 3 (starting at 18 hours), and quantified on day 4. The number of bacteria was determined by spectrophotometric absorbance or optical density (OD) at 600 nm. The five phases of the experiment were: pellicle formation; bacterial attachment; biofilm growth; exposure to actives; and bacterial enumeration.

To form the pellicles, HA Discs were ultrasonically washed in deionized water and air-dried, then autoclaved. The discs were placed in a 24 well plate with 1 ml 50% sterile saliva (1 part sterile whole saliva: 1 part saliva buffer, filter sterilize after preparation) for 2 hours with slow agitation at room temperature. The saliva was suctioned and then the discs were transferred to fresh wells for bacterial attachment.

The discs were inoculated with salivary bacteria by one of two methods: (1) incubation with saliva bacteria suspended in 50% saliva at a standard OD for 2-h at 37° C.; after the attachment phase the discs are transferred to supplemented saliva growth medium, or (2) direct addition of bacteria with media and incubation.

To form the biofilms, the bacterial suspension was removed, and the discs were transferred to fresh wells. One ml of supplemented saliva medium was added and the plate was placed in the incubator for overnight incubation and for the duration of the experiment (up to 72 hours).

A stock solution of 1% Magnolia Bark Extract in 60% ethanol was prepared. Magnolia Bark Extract samples were prepared having a concentration range of 125, 250, 500, and 1000 μg/ml (ppm) in a Phosphate-Buffered-Saline (PBS) solution, where the negative control was PBS and the positive control was CHX having a concentration of 0.12%. The PBS control solution had a composition as shown below in Table 4.

TABLE 4

Phosphate Buffered Saline Composition

| Ingredient | g/L |
| --- | --- |
| NaCl | 8.0 |
| KCl | 0.2 |
| $Na_2PO_4$ | 1.44 |
| $KH_2PO_4$ | 0.24 |

One ml quantities of active ingredients and controls were placed into fresh wells, and the discs transferred to these wells for 5 minutes. The chlorhexidine control exposure was one minute, two times a day to mimic the standard mouth-rinse procedure. The exposure to active ingredient was carried out at 8:00 AM, 12:00 and 4:00 PM. After the timed exposure, the solution was removed and the discs washed twice with PBS and then transferred to fresh medium. For some experiments, the medium used during the day was Tryptic Soy Broth (TSB) with a 50 μl 40% sterile sucrose solution added to each well (to give a 2% sucrose solution). The medium was not replaced after the mid-day exposure.

After overnight incubation (day 2), discs were exposed to controls and actives. On day 3 the biofilms were again exposed to tests and controls. On day 4 the discs were removed from the medium, the medium pH was measured to obtain an indication of metabolic activity, and the discs were placed into tubes with 2.5 ml PBS, vortexed for 20s, and then placed into the ultrasonic bath for another 20 sec. The suspension was transferred into cuvettes and the bacterial cell density determined by OD measurements at 600 nm.

The results of the pH measurements are shown below in Table 5 and the percentage reductions in OD compared to PBS control are shown below in Table 6.

TABLE 5 pH Measurements

| Test Sample | pH |
| --- | --- |
| PBS Control | 5.4 |
| CHX Control | 8.8 |
| MBE 125 | 5.2 |
| MBE 250 | 6.0 |
| MBE 500 | 7.1 |
| MBE 1000 | 7.6 |

TABLE 6

Percentage Reductions in Optical Density at 600 nm

| Test Sample | % OD reduction |
| --- | --- |
| PBS Control | 0 |
| CHX Control | 84 |

TABLE 6-continued

Percentage Reductions in Optical Density at 600 nm

| Test Sample | % OD reduction |
| --- | --- |
| MBE 125 ppm | −2 |
| MBE 250 ppm | 21 |
| MBE 500 ppm | 53 |
| MBE 1000 ppm | 59 |

The results shown above in Tables 5 and 6 illustrate a clear effect and dose-response of Magnolia Bark Extract on inhibition of biofilm metabolic activity (as determined by pH of the medium) and biofilm formation (OD). Chlorhexidine had a strong inhibitory effect on plaque metabolism and cell number. Magnolia Bark Extract was less effective than chlorhexidine, but the chlorhexidine concentration was slightly higher than the Magnolia Bark Extract.

To evaluate the effect of Magnolia Bark Extract in combination with the surface active agent, sodium lauryl sulfate, five active ingredient solutions were prepared using the procedures described above. The chlorhexidine control solution was prepared having a slightly reduced concentration of 0.1% (1000 ppm). Also, the MBE solutions were prepared to have a concentration of 500 ppm. Sodium lauryl sulfate was added to two of the Magnolia Bark Extract solutions to obtain SLS concentrations of 0.05% and 0.1% in the Magnolia Bark Extract solutions. The testing with Magnolia Bark Extract described above was repeated with the five solutions.

The pH test results are shown below in Table 7, where sodium lauryl sulfate is designated as "SLS."

TABLE 7 pH Measurements

| Test Sample | pH |
| --- | --- |
| PBS Control | 4.9 |
| CHX Control | 8.8 |
| SLS 1000 ppm | 5.7 |
| MBE 500 ppm | 7.1 |
| MBE 500 ppm/SLS 500 ppm | 5.9 |
| MBE 500 ppm/SLS 1000 ppm | 6.2 |

The percentage reductions in optical density (OD) test results are shown below in Table 8. Note that the data in the last row of this table were taken from a different experiment.

TABLE 8

Percentage Reduction in Optical Density at 600 nm

| Test Sample | % OD reduction |
| --- | --- |
| PBS Control | 0 |
| CHX Control | 94 |
| SLS 1000 ppm | 61 |
| MBE 500 ppm | 65 |
| MBE 500 ppm/SLS 500 ppm | 79 |
| MBE 500 ppm/SLS 1000 ppm | 70 |
| MBE 1000 ppm/SLS 500 ppm | 88 |

The results listed above in Tables 7 and 8 show that the chlorhexidine control had the highest pH and this control also had the lowest OD. Based on pH data (an indication of metabolic activity), 500 ppm Magnolia Bark Extract alone showed greater metabolic inhibition than the sodium lauryl sulfate or the Magnolia Bark Extract/sodium lauryl sulfate mixtures. The OD absorbance data (bacterial number), however, indicates a synergistic effect at reducing the biofilm in test solutions combining Magnolia Bark Extract and sodium lauryl sulfate. In particular, the results show that the 1000 ppm sodium lauryl sulfate and 500 ppm Magnolia Bark Extract had similar effects in terms of plaque quantity, although Magnolia Bark Extract inhibited plaque metabolic activity to a greater extent. The Magnolia Bark Extract with sodium lauryl sulfate at 500 ppm reduced plaque growth compared to 500 ppm Magnolia Bark Extract alone. Further, the sodium lauryl sulfate at 1000 ppm was less effective than at 500 ppm in combination with 500 ppm Magnolia Bark Extract. The most effective combination was 1000 ppm of Magnolia Bark Extract in combination with 500 ppm of sodium lauryl sulfate.

Although not wishing to be bound by any particular theory regarding the active mechanism of the invention, it is possible that the reason for the paradoxical effect of decreased cell mass with increased metabolic activity of the Magnolia Bark Extract/sodium lauryl sulfate mixtures relates to the action of the sodium lauryl sulfate in allowing more rapid penetration of the Magnolia Bark Extract into the biofilm, where it has an immediate germ kill and/or growth-inhibitory effect, but the Magnolia Bark Extract is also rinsed away more easily, so the substantivity and prolonged metabolic effect is minimized.

To evaluate the germ-kill efficacy and synergist effect when two or more germ-kill actives are combined, testing was performed to determine the ratio of MBE to surface active agent. The germ-kill active and/or surface active agent was dissolved in ethanol or sterile water to give an initial concentration 0.1% to 1%. The solution was diluted with a nutrient broth to give an initial concentration 0.05% to 0.5%, which was then serially diluted two-fold so that each subsequent dilution contained 50% of the compound concentration of the previous dilution while maintaining a constant level of nutrients for each dilution. These dilutions were inoculated with representative oral microorganisms, or incubated saliva, and incubated for 24 hours at 37° C. For each surface active agent, the lowest dilution that was not turbid was registered as the MIC. The MBC was determined by transferring 10 microliter of liquid from non-turbid tubes to fresh growth media and incubated for 48 hrs. For each surface active agent, the lowest dilution that did not demonstrate growth was considered the MBC.

Table 9 below shows the MIC of various surface active agents and emulsifiers on incubated saliva.

TABLE 9

Minimum-Inhibitory-Concentration of Selected Surface active agents

| Sample | MIC (ppm) |
| --- | --- |
| Sodium Lauryl Sulfate | 50 |
| Betaine BF-20 | >1000 |
| Tego Betain CKD | 25 |
| Tego Betain ZF | 25 |
| Sodium Brasslate | 500 |
| Sodium Lauroyl Sarcosinate | 100 |
| Sodium Stearoyl Lactylate | >3000 |
| Tween 20 | >1000 |
| Sucrose Stearate | >500 |
| Sucrose Distearate | >500 |
| Chlorhexidine gluconate* | 2 |

*as a positive control

The results show sodium lauryl sulfate, Cocamidopropyl Betaine, are good germ-kill surface active agents, while sodium brasslate shows a moderate germ-kill efficacy. Sodium stearoyl lactylate, Polysorbate 20 (commonly known as Tween 20), Sucrose stearate, and Sucrose distearate are weak or non germ-kill actives.

To evaluate the synergistic effect of an active ingredient in combination with a surface active agent, the fractional inhibitory index (FIC) was computed according to equation (1) below:

$$FIC = [MIC_{A\text{-combined with }B}/MIC_{A\text{-alone}} + MIC_{B\text{-combined with }A}/MIC_{B\text{-alone}}] \quad (1)$$

where an FIC value of less than 1.0 is synergistic, an FIC between 1.0 and 2.0 is additive, and an FIC greater than 2.0 is antagonistic.

Table 10 below shows the MIC values for combinations of Magnolia Bark Extract/sodium lauryl sulfate and Magnolia Bark Extract/Tween-20 on *S. mutans*:

TABLE 10

Minimum-Inhibitory-Concentration of Selected Surface Active Agents

| Sample | MIC/ppm | FIC |
| --- | --- | --- |
| Sodium Lauryl Sulfate | 100 | — |
| Magnolia Bark Extract | 25 | — |
| MBE/SLS 1/4 | 50 | 1 |
| MBE/SLS 3/2 | 25 | 0.70 |
| MBE/SLS 4/1 | 25 | 0.85 |
| MBE/Tween 20 100/100 | 25 | 1 |
| MBE/Tween 20 100/250 | >100 | >2 |
| MBE/Tween 20 100/500 | >100 | >2 |
| Chlorhexidine gluconate* | 2 | — |

The results indicate that Magnolia Bark Extract and sodium lauryl sulfate show synergistic effect (FIC<1) when combined in a ratio (MBE/SLS) between about 1/4 to about 4/1. However, Magnolia Bark Extract and Tween-20 show antagonist effect (FIC>2) when combined.

In particular, the results show that certain ratios of Magnolia Bark Extract to sodium lauryl sulfate show synergistic effects. Accordingly, the present invention contemplate oral compositions that contain a synergistic ratio of Magnolia Bark Extract to a surface active agent. From the foregoing experimental results, Magnolia Bark Extract in combination with a surface active agent will produce a synergistic anti-microbial effect in an oral composition. Oral compositions having a surface active agent in a concentration range of about 25 ppm to about 500 ppm in combination with Magnolia Bark Extract show synergistic properties for inhibiting the biofilm formation that leads to dental plaque. Further, oral compositions having a weight ratio of at least about one part Magnolia Bark Extract to one part surface active agent will produce a synergistic anti-microbial effect in an oral composition. Further, the synergistic ratio of Magnolia Bark Extract to surface active agent can range from about 1 part Magnolia Bark Extract to 1 part surface active agent up to about 4 parts Magnolia Bark Extract to 1 part surface active agent. Most preferably, the synergistic ratio is about 2 parts Magnolia Bark Extract to 1 part surface active agent. Accordingly, the present invention contemplates a wide range of oral compositions containing a synergistic combination of Magnolia Bark Extract and a surface active agent.

EXAMPLES

The examples listed below are not intended to exclude other variations in formulations and the present invention is not limited to these formulations.

Chewing Gum Formulations

In an aspect of the present invention, an effective amount for anti-microbial benefit of Magnolia Bark Extract in combination with a surface active agent, such as described above, is present in a chewing gum formulation. In another aspect of the present invention, the amount of Magnolia Bark Extract is present in an amount up to 5% by weight of the chewing gum product. In yet an aspect of the present invention, the amount of Magnolia Bark Extract is 1% of the weight of the chewing gum product. In still another aspect, the Magnolia Bark Extract is present in the amount of 0.01% by weight of the chewing gum product. Considering the potency of Magnolia Bark Extract as described in the in vitro studies above, levels as low as 0.005% by weight of the chewing gum product should be effective in bactericidal properties. Accordingly, an effective amount of Magnolia Bark Extract can range between about 0.005% by weight to about 5% by weight of the composition. The absolute amount of sodium lauryl sulfate in the chewing gum formulation can range from about 4 mg to about 10 mg.

In general, a chewing gum composition typically comprises a water-soluble bulk portion, a water-insoluble chewable gum base portion and typically water-soluble flavoring agents. The water-soluble bulk portion dissipates with a portion of the flavoring agent over a period of time during chewing. The gum base portion is retained in the mouth throughout the chew.

The insoluble gum base generally comprises elastomers, resins, fats and oils, softeners and inorganic fillers. The gum base may or may not include wax. The insoluble gum base can constitute approximately 5% to about 95% by weight of the chewing gum, more commonly the gum base comprises 10% to about 50% of the gum, and in some preferred embodiments approximately 25% to about 35% by weight, of the chewing gum.

In a particular embodiment, the chewing gum base of the present invention contains about 20% to about 60% by weight synthetic elastomer, up to about 30% by weight natural elastomer, about 5% to about 55% by weight elastomer plasticizer, about 4% to about 35% by weight filler, about 5% to about 35% by weight softener, and optional minor amounts (about 1% or less by weight) of miscellaneous ingredients such as colorants, antioxidants, etc.

Synthetic elastomers may include, but are not limited to, polyisobutylene with GPC weight average molecular weight of about 10,000 to about 95,000, isobutylene-isoprene copolymer (butyl elastomer), styrenecopolymers having styrene-butadiene ratios of about 1:3 to about 3:1, polyvinyl acetate having GPC weight average molecular weight of about 2,000 to about 90,000, polyisoprene, polyethylene, vinyl acetate vinyl laurate copolymer having vinyl laurate content of about 5% to about 50% by weight of the copolymer, and combinations thereof.

Preferred ranges for polyisobutylene are 50,000 to 80,000 GPC weight average molecular weight; for styrene are 1:1 to 1:3 bound styrene; for polyvinyl acetate are 10,000 to 65,000 GPC weight average molecular weight, with the higher molecular weight polyvinyl acetates typically used in bubble gum base; and for vinyl acetate laurate, a vinyl laurate content of 10.

Natural elastomers may include natural rubber, such as smoked or liquid latex and guayule, as well as natural gums, such as jelutong, lechi caspi, perillo, sorva, massaranduba balata, massaranduba chocolate, nispero, rosindinha, chicle, gutta hang kang, and combinations thereof. The preferred synthetic elastomer and natural elastomer concentrations vary depending on whether the chewing gum in which the base is used is adhesive or conventional, bubble gum or regular gum, as discussed below. Preferred natural elastomers include jelutong, chicle, sorva and massaranduba balata.

Elastomer plasticizers may include, but are not limited to, natural rosin esters such as glycerol esters or partially hydrogenated rosin, glycerol esters of polymerized rosin, glycerol esters of partially dimerized rosin, glycerol esters of rosin, pentaerythritol esters of partially hydrogenated rosin, methyl and partially hydrogenated methyl esters of rosin, pentaerythritol esters of rosin; synthetics such as terpene resins derived from alpha, beta, and/or any suitable combinations of the foregoing. The preferred elastomer plasticizers will also vary depending on the specific application, and on the type of elastomer which is used.

Fillers/texturizers may include magnesium and calcium carbonate, ground limestone, silicate types such as magnesium and aluminum silicate, clay, alumina, talc, titanium oxide, mono-, di- and tri-phosphate, cellulose polymers, such as wood, and combinations thereof.

Softeners/emulsifiers may include tallow, hydrogenated tallow, hydrogenated and partially hydrogenated vegetable oils, cocoa butter, glycerol monostearate, glycerol triacetate, lecithin, mono and triglycerides, acetylated monoglycerides, fatty acids (for example stearic, pamitic, oleic and linoleic acids), and combinations thereof.

Colorants and whiteners may include FD&C dyes and lakes, fruit and vegetable extracts, titanium dioxide, and combinations thereof.

The base may or may not include wax. An example of a wax-free gum base is disclosed in U.S. Pat. No. 5,286,500, the disclosure of which is incorporated herein by reference.

In addition to a water insoluble gum base portion, a typical chewing gum composition includes a water soluble bulk portion and one or more flavoring agents. The water soluble portion can include bulk sweeteners, high intensity sweeteners, flavoring agents, softeners, emulsifiers, colors, acidulants, fillers, antioxidants, and other components that provide desired attributes.

Softeners are added to the chewing gum in order to optimize the chewability and mouthfeel of the gum. The softeners, which are also known as plasticizers and plasticizing agents, generally constitute between approximately 0.5% to about 15% by weight of the chewing gum. The softeners may include glycerin, lecithin, and combinations thereof. Aqueous sweetener solutions such as those containing sorbitol, hydrogenated starch hydrolysates, corn syrup and combinations thereof, may also be used as softeners and binding agents in chewing gum.

Bulk sweeteners, or bulking agents, include both sugar and sugarless components. Bulk sweeteners typically constitute about 5% to about 95% by weight of the chewing gum, more typically, about 20% to about 80% by weight, and more commonly, about 30% to about 60% by weight of the gum. Sugar sweeteners generally include saccharide components commonly known in the chewing gum art, including but not limited to, sucrose, dextrose, maltose, dextrin, dried invert sugar, fructose, levulose, galactose, corn syrup solids, and the like, alone or in combination. Sugarless sweeteners include, but are not limited to, sugar alcohols such as sorbitol, mannitol, xylitol, hydrogenated starch hydrolysates, maltitol, and the like, alone or in combination.

High intensity artificial sweeteners can also be used, alone or in combination, with the above. Preferred sweeteners include, but are not limited to, sucralose, aspartame, NAPM derivatives such as neotame, salts of acesulfame, altitame, saccharin and its salts, cyclamic acid and its salts, glycyrrhizinate, dihydrochalcones, thaumatin, monellin, and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extension may be used to achieve the desired release characteristics.

Combinations of sugar and/or sugarless sweeteners may be used in chewing gum. Additionally, the softener may also provide additional sweetness such as with aqueous sugar or alditol solutions.

If a low calorie gum is desired, a low caloric bulking agent can be used. Examples of low caloric bulking agents include: polydextrose; raftilose, raftilin; fructooligosaccharides (NutraFlora); Palatinose oligosaccharide; guar gum hydrolysate (Sun Fiber); or indigestible dextrin (Fibersol). However, other low calorie bulking agents can be used.

A variety of flavoring agents can also be used, if desired. The flavor can be used in amounts of about 0.1 to about 15 weight percent of the gum, and preferably, about 0.2% to about 5% by weight. Flavoring agents may include essential oils, synthetic flavors or mixtures thereof including, but not limited to, oils derived from plants and fruits such as citrus oils, fruit essences, peppermint oil, spearmint oil, other mint oils, clove oil, oil of wintergreen, anise and the like. Artificial flavoring agents and components may also be used. Natural and artificial flavoring agents may be combined in any sensorially acceptable fashion. Flavoring may include a cooling agent to enhance the flavor and perceived breath freshening of the product. Cooling agents include menthol, ethyl p-menthane carboxamide, N,2,3-trimethyl-2-isopropyl-butanamide, menthyl glutarate (Flavor Extract Manufacturing Association (FEMA 4006)), menthyl succinate, menthol PG carbonate, menthol EG carbonate, menthyl lactate, menthone glyceryl ketal, menthol glyceryl ether, N-tertbutyl-p-menthane-3-carboxamide, p-menthane-3-carboxylic acid glycerol ester, methyl-2-isopryl-bicyclo (2.2.1), heptane-2-carboxamide, menthol methyl ether and combinations thereof.

In addition to the Magnolia Bark Extract and surface active agents of the present invention, additional active ingredients or medicaments may be added for various purposes. If the medicament or active is water soluble in the chewing gum, it preferably will include a base/emulsifier system which leads to the desired concentration of the medicament in the saliva (more hydrophilic balance). If the medicament or active is water insoluble, the chewing gum preferably includes a base/emulsifier system which leads to the desired concentration of the medicament in the saliva (more lipophilic balance).

In manufacturing the chewing gum including the active agent or ingredient, the active agent or medicament is added, preferably, early on in the mix. The smaller the amount of active ingredient used, the more necessary it becomes to preblend that particular ingredient to assume uniform distribution throughout the batch of gum. Whether a preblend is used or not, the active agent or medicament should be added within the first five minutes of mixing. For faster release, the active agent may be added late in the process.

Optionally, the chewing gum of the present invention may include additional breath freshening, anti microbial or oral health ingredients, such as food acceptable metallic salts selected from zinc and copper salts of gluconic acid, zinc and copper salts of lactic acid, zinc and copper salts of acetic acid, zinc and copper salts of citric acid, copper chlorophyll and combinations thereof. Further, anti-microbial essential oils and flavor components such as peppermint, methyl salicylate, thymol, eucalyptol, cinnamic aldehyde, polyphosphate, pyrophosphate and combinations thereof may be added to the gum composition. Dental health ingredients, such as fluoride salts, phosphate salts, proteolytic enzymes, lipids, anti-microbials, calcium, electrolytes, protein additives, dental abrasives and combinations thereof may also be added to the gum composition.

In general, chewing gum is manufactured by sequentially adding the various chewing gum ingredients to a commercially available mixer known in the art. After the ingredients have been thoroughly mixed, the gum mass is discharged from the mixer and shaped into the desired form such as rolling sheets and cutting into sticks, extruding into chunks or casting into pellets, which are then coated or panned.

Generally, the ingredients are mixed by first melting the gum base and adding it to the running mixer. The base may also be melted in the mixer itself. Color or emulsifiers may also be added at this time. A softener such as glycerin may also be added at this time, along with syrup and a portion of the bulking agent. Further parts of the bulking agent are added to the mixer. Flavoring agents are typically added with the final portion of the bulking agent. Other optional ingredients are added to the batch in a typical fashion, well known to those of ordinary skill in the art.

The entire mixing procedure typically takes from five to fifteen minutes, but longer mixing times may sometimes be required. Those skilled in the art will recognize that many variations of the above described procedure may be followed.

Chewing gum base and chewing gum product have been manufactured conventionally using separate mixers, different mixing technologies and, often, at different factories. One reason for this is that the optimum conditions for manufacturing gum base, and for manufacturing chewing gum from gum base and other ingredients such as sweeteners and flavors, are so different that it has been impractical to integrate both tasks. Chewing gum base manufacture, on the one hand, involves the dispersive (often high shear) mixing of difficult-to-blend ingredients such as elastomer, filler, elastomer plasticizer, base softeners/emulsifiers and sometimes wax, and typically requires long mixing times. Chewing gum product manufacture, on the other hand, involves combining the gum base with more delicate ingredients such as product softeners, bulk sweeteners, high intensity sweeteners and flavoring agents using distributive (generally lower shear) mixing, for shorter periods.

Table 11 below lists examples of formulations of Magnolia Bark Extract in chewing gum. Example 1 is a comparative example of a prior art gum formulation.

TABLE 11

Antimicrobial Gum Formulas
(dry weight percent basis)

| Ingredient | Example 1 | Example 2 | Example 3 | Example 4 | Example 5 |
|---|---|---|---|---|---|
| Gum Base | 25.21 | 26.22 | 25.21 | 24.21 | 25.21 |
| Lecithin | 0.17 | 0.17 | 0.17 | 2.00 | 0.17 |
| NaHCO$_3$ | 0.25 | 0.25 | 0.25 | 0.25 | 0.25 |
| Sorbitol | 50.86 | 49.86 | 47.86 | 45.86 | 50.36 |
| MBE | — | 0.10 | 3.00 | 2.00 | 0.50 |
| Mannitol | 4.25 | 4.25 | 4.25 | 4.25 | 4.25 |
| Lycasin/Glycerin | 8.51 | 8.51 | 8.51 | 8.68 | 8.51 |
| Glycerin | 8.50 | 8.50 | 8.50 | 8.50 | 8.50 |
| Encapsulated Sweetener | 0.67 | 0.67 | 0.67 | 0.67 | 0.67 |
| Flavor | 1.58 | 1.58 | 1.58 | 1.58 | 1.58 |
| Total | 100.00 | 100.00 | 100.00 | 100.00 | 100.00 |

In accordance with the invention, each of the formulations in examples 2-5 is supplemented with a surface active agent as described above. In one exemplary embodiment, each of the examples 2-5 includes about 0.001% to about 2% of a surface active agent as described above. In another exemplary embodiment, each of the examples 2-5 includes about 0.001% to about 2.0% of a surface active agent as described above. In yet another exemplary embodiment, each of the examples 2-5 includes about sodium lauryl sulfate and Magnolia Bark Extract in a ratio of about 1/4 to about 4/1.

Edible Film Formulations

In an aspect of the present invention, an effective amount for anti-microbial benefit of Magnolia Bark Extract in combination with a surface active agent, such as described above, is present in an edible film formulation. In another aspect of the present invention, the amount of Magnolia Bark Extract is present in an amount up to 10% by weight of the edible film formulation. In yet another aspect of the present invention, the amount of Magnolia Bark Extract is about 8% of the weight of the edible film product. In still another aspect, the Magnolia Bark Extract is present in the amount of about 5% by weight of the edible film product. Considering the potency of Magnolia Bark Extract as described in the in vitro studies above, about 1% by weight of the edible film product may also be effective in bactericidal properties. Accordingly, an effective amount of Magnolia Bark Extract can range between about 1% by weight to about 10% by weight of the composition. The absolute amount of sodium lauryl sulfate in the edible film formulation can range from about 4 mg to about 10 mg.

The present invention provides edible film formulations for oral mucoadhesion and methods of using and making same. In particular, the edible films of the present invention include at least three types of film forming agents other than pullulan.

Applicants have uniquely discovered that the use of a mixture of at least three types of film forming agents, such as maltodextrins, fillers (for example, microcrystalline cellulose (MCC)) and hydrocolloids (for example, sodium aliginate), can be effectively utilized to prepare stand alone edible films. The edible films are composed of ingredients that are readily available, can be prepared at lower costs and display similar properties as compared to edible films composed of pullulan. In this regard, the edible films can provide a physiologically acceptable film, which is suitably adapted to adhere to oral surfaces of an oral cavity and rapidly dissolve therein.

The edible films of the present invention can be utilized to deliver or release oral care agent(s). Such agents include anti-microbial agents and salivary stimulants to treat, for example, halitosis, dental plaque, gingivitis, xerostomia, dry mouth, like oral conditions or combinations thereof. Further, the oral care edible film can act as a breath freshener effective against malodor.

The oral cleansing and breath freshening effects of the edible film of the present invention can be achieved by entrapping the oral care agents within the oral cavity to provide extended efficacy. In this regard, the highly dissolvable edible film can act as a medium through which a pharmaceutically active oral agent can be administered via a mucous membrane of the oral cavity.

Further, the edible films can include a variety of other suitable ingredients, such as softeners, colorants, flavoring agents, emulsifiers, surface active agents, thickening agents, binding agents, sweeteners, fragrances, other like ingredients or combinations thereof.

In an embodiment, the edible films preferably include a mixture of at least three types of film forming agents, such as maltodextrins, fillers and hydrocolloids. It should be appreciated that the edible film of the present invention can be composed of one or more different compounds associated with each of the at least three types of film forming agents.

In an embodiment, the maltodextrin component constitutes between about 5% to about 60% by dry weight of the edible film, preferably about 20% to about 40% by dry weight. The maltodextrin component can be processed in any suitable way.

The hydrocolloid can provide thickness and decrease brittleness of the edible films. The hydrocolloid can include any suitable type, amount and number of hydrocolloids. In an embodiment, the hydrocolloid can constitute between about 10% to about 50% by dry weight of the edible film, preferably about 20% to about 30% by dry weight. The hydrocolloid can be derived from, for example, natural seaweeds, natural seed gum, natural plant exudates, natural fiber extracts, biosynthetic gums, gelatins, biosynthetic process starch or cellulosic materials, alginates, sodium alginate, calcium alginate, carrageenans, guar gum, locust gum, tara gum, gum arabic, ghatti gum, agar gum, xanthan gum, pectin, other like hydrocolloid source material or combinations thereof.

Any suitable food-grade bulk filler can also be added to the edible film. This can reduce any slimy texture as well as provide structure to the film thereby making it more palatable. In an embodiment, the filler can constitute about 5% to about 30% by dry weight of the film, preferably about 15% to about 25% by dry weight. The filler can include, for example, microcrystalline cellulose, cellulose polymers, such as wood, magnesium and calcium carbonate, ground limestone, silicates, such as magnesium and aluminum silicate, clay, talc, titanium dioxide, mono-calcium phosphate, di-calcium phosphate, tri-calcium phosphate, other like bulk fillers or combinations thereof.

It is believed that the unique mixture of at least three film forming agents other than pullulan, for example, a maltodextrin, a hydrocolloid and a bulk filler, can provide a stand alone edible film composition which exhibits many of the same desirable properties exhibited by more expensive pullulan-based edible film. Applicants have desirably discovered that the pullulan-free edible film formulation of the present invention can exhibit, for example, clean mouth feel, clean favor and ease of manufacture similar to currently available pullulan-based films.

As previously discussed, a variety of other suitable ingredients can be added to the edible film of the present invention. For example, any suitable medicament for oral cleansing, breath freshening or the like can be added to the film formulation. The medicaments can include, for example, a pH control agent, such as urea and buffers, inorganic components for tartar or caries control, such as phosphates and fluorides, a breath freshening agent such as zinc gluconate, an anti-plaque/anti-gingivitis agent, such as cholorhexidene, CPC, and triclosan, a saliva stimulating agent including, for example, food acids such as citric, lactic, maleic, succinic, ascorbic, adipic, fumaric and tartaric acids, a pharmaceutical agent, a nutraceutical agent, a vitamin, a mineral, other like medicaments or combinations thereof.

The medicaments can be delivered or released into the oral cavity for effective oral treatment, such as oral cleansing and/or breath freshening. In this regard, the film forming agent of the edible film can act to entrap the medicaments within the oral cavity thereby providing extended efficacy thereof. In doing so, it is believed that the pullulan-free edible film compositions of the present invention more uniformly release the medicament into the oral cavity for absorption via open wounds or mucous membrane in a greater manner than could be previously achieved. Moreover, it is also believed that the mixture of film forming agents of the present invention can entrap the medicament within the oral cavity for an extended period of time to prolong and enhance the effects of the medicament. In addition, by extending the contact time of the medicament within the oral cavity, the medicament is absorbed to a greater extent thereby increasing its bioavailability.

If reduced levels of film forming agents are utilized, softeners can be used to reduce the brittleness of the resulting films. The softeners, which are also known as plasticizers or plasticizing agents, generally constitute about up to 20% by dry weight of the film, preferably about 2% to about 10% by dry weight. The softeners can include plasticizers containing, for example, sorbitol and other polyols, glycerin, polyethylene glycol, propylene glycol, hydrogenated starch hydrolysates, corn syrups, other like material or combinations thereof.

The edible film formulations of the present invention can also include colorants or coloring agents which can be used in any suitable amount to produce the desired color. Coloring agents can include, for example, natural food colors and dyes suitable for food, drug and cosmetic applications. The colorants are typically knows as FD&C dyes and lakes.

A variety of flavoring agents can also be added to the edible films. Any suitable amount and type of artificial and/or natural flavoring agents can be used in any sensorially acceptable fashion. For example, the flavor can constitute about 0.1% to about 20% by dry weight of the film, preferably about 10% to 15%. The flavoring agent can include, for example, essential oils, synthetic flavors or mixtures including but not limited to oils delivered from plants and fruits such as citrus oils, fruit essences, peppermint oil, spearmint oil, other mint oils, clove oils, oil of wintergreen, anise and the like, flavor oils with germ killing properties such as menthol, eucalyptol, thymol, like flavoring agents or combinations thereof.

The flavor can be enhanced and evenly distributed throughout the product by emulsification. Any suitable amount and type of natural and/or synthetic food grade emulsifier can be used. For example, the emulsifier can include lecithin, food-grade non-ionic emulsifiers, such as fatty acids ($C_{10}$-$C_{18}$), mono and diacyl glycerides, ox bile extract, polyglycerol esters, polyethylene sorbitan esters, propolyene glycol, sorbitan monopalmitate, sorbitan monosterate, sorbitan tristearate, enzyme modified lecithin, hyroxylated lecithins, other like emulsifiers or combinations thereof.

The flavors can be emulsified by any suitable emulsification process, such as mechanical processing, vigorous stirring, intense pressure fluctuations that occur in turbulent flow such as homogenization, sonication, colloid milling and the like.

The present invention provides methods of producing the edible film formulations. In general, the edible film formulations are prepared by forming a base solution that includes at least three types of film forming agents, such as maltodextrins, hydrocolloids and fillers and processing the base solution to form an edible film. Typically, the base solution is prepared by adding an initial mixture of dry ingredients to water that is stirred.

To the base solution, additional ingredients, such as flavor/emulsifier blends, sweeteners, softeners, color, the like or combinations thereof, can be added. In an embodiment, the solution is stirred continuously and heated at a temperature ranging from about 40° C. to about 60° C. The solution then can be dried in any suitable manner, thereby forming the edible film.

It should be appreciated that any suitable type, number and arrangement of process procedures or steps (i.e., mixing, heating, drying, cooling, addition of ingredients), process parameters (i.e., temperature, pressure, pH, process times) or the like can be utilized.

By way of example and not limitation, the following examples in Tables 12 and 13 below illustrate various embodiments of the edible film formulations of the present invention.

TABLE 12

Antimicrobial Edible Film Formulations
(dry weight percent)

| Ingredient | Example 6 | Example 7 | Example 8 | Example 9 | Example 10 |
|---|---|---|---|---|---|
| Maltodextrin | 25.81 | 47.75 | 33.2 | 40.70 | 18.05 |
| Sodium Alginate | 22.00 | — | 18.00 | — | 12.00 |
| Calcium Alginate | — | 13.90 | — | 14.50 | — |
| Carageenan | — | — | — | — | 12.00 |
| Microcrystalline Cellulose | 25.75 | 9.00 | 18.85 | 13.45 | 20.00 |
| Calcium Carbonate | — | 2.45 | — | — | — |
| Glycerin | 12.25 | 10.00 | 8.00 | — | 9.5 |
| Sorbitol | — | — | — | 6.00 | 1.55 |
| Propylene Glycol | — | — | 3.65 | 5.00 | — |
| Menthol | 1.00 | 0.05 | — | 1.25 | — |
| Eucalyptol | — | 0.05 | — | 1.00 | — |
| Maleic Acid | — | — | — | — | 1.35 |
| Citric Acid | — | — | 1.25 | — | 1.00 |
| Chlorhexidine | 0.24 | — | — | 1.00 | — |
| Triclosan | — | 2.25 | — | 1.00 | — |
| Flavor | 9.40 | 11.00 | 12.00 | 14.00 | 10.00 |
| High Intensity Sweetener | 1.50 | 1.25 | 1.00 | 1.05 | 1.45 |
| MBE | 1.00 | 2.25 | 2.00 | 0.50 | 10.00 |
| Color | 0.05 | 0.05 | 0.05 | 0.05 | 0.10 |
| Sodium Lauryl Sulfate | 1.00 | — | 2.00 | 0.50 | 3.00 |
| Total | 100.00 | 100.00 | 100.00 | 100.00 | 100.00 |

In accordance with the invention, each of the formulations in examples 6-10 is supplemented with a surface active agent as described above.

TABLE 13

Antimicrobial Edible Film Formulations
(dry weight percent basis)

| Ingredient | Example 11 | Example 12 | Example 13 | Example 14 | Example 15 |
|---|---|---|---|---|---|
| Maltodextrin | 35.00 | 32.30 | 28.15 | 32.50 | 30.00 |
| Sodium Alginate | 22.15 | 19.10 | 17.00 | 28.15 | — |
| Carageenan | — | — | — | — | 20.15 |
| Microcrystalline Cellulose | 20.00 | 18.00 | 17.00 | 17.00 | 18.00 |
| Gum Arabic | — | — | 11.00 | — | — |
| Glycerin | 7.30 | 15.00 | 7.30 | 7.30 | 7.30 |
| Flavor | 11.00 | 11.00 | 11.00 | 11.00 | 11.00 |
| Lecithin | 2.00 | 0.05 | 2.00 | 2.00 | 2.00 |
| High Intensity Sweetener | 1.50 | 1.50 | 1.50 | 1.50 | 1.50 |
| MBE | 1.00 | 3.00 | 5.00 | 0.50 | 10.0 |
| Color | 0.05 | 0.05 | 0.05 | 0.05 | 0.05 |
| Total | 100.00 | 100.00 | 100.00 | 100.00 | 100.00 |

In accordance with the invention, each of the formulations in examples 6-15 is supplemented with a surface active agent as described above. In one exemplary embodiment, each of the examples 6-15 includes about 0.01 to about 2% a surface active agent as described above. In another exemplary embodiment, each of the examples 6-15 includes about 0.001% to about 2.0% of a surface active agent as described above. In yet another exemplary embodiment, each of the examples 6-15 includes sodium lauryl sulfate and Magnolia Bark Extract in a ratio of about 1/4 to about 4/1.

Confectionary Formulations

In an aspect of the present invention, an effective amount for anti-microbial benefit of Magnolia Bark Extract is present in combination with a surface active agent, such as described above, in a confectionery formulation. In another aspect of the present invention, the amount of Magnolia Bark Extract is present in an amount up to 3% by weight of the confectionery product. In yet another aspect of the present invention, the amount of Magnolia Bark Extract is 1% of the weight of the confectionery product. In still another aspect, the Magnolia Bark Extract is present in the amount of 0.01% by weight of the confectionery product. Considering the potency of Magnolia Bark Extract as described in the in vitro studies above, 0.005% by weight of the confectionery product is also effective in bactericidal properties. Accordingly, an effective amount of Magnolia Bark Extract can range between about 0.005% by weight to about 3% by weight of the composition. The absolute amount of sodium lauryl sulfate in the confectionery formulation can range from about 4 mg to about 10 mg.

Confectionery products for this invention may be hard candies, chewy candies, coated chewy center candies and tabletted candies. By way of example, the hard candy is primarily comprised of corn syrup and sugar, and derives its name from the fact that it contains only 1.0% and 4% moisture. In appearance, these types of candies are solid, but they are actually supercooled liquids, which are far below their melting points. There are different types of hard candies. Glass types are usually clear or made opaque with dyes; and Grained types, which are always opaque.

The continuous process of making the deposited glass types with a sugar base are as follows. Corn syrup is spread over a cylinder heated by high pressure steam. Rapid heat exchange causes the water in the syrup to evaporate. The cooked syrup is discharged, colors and flavors are added. The syrup is cooled and deposited onto a stainless steel conveyor. The syrup can be conveyed directly to hoppers which then discharge directly into molds.

The candy is conveyed to batch rollers, which shapes and sizes the batch. The candy enters a former, which shapes the individual pieces into discs, balls, barrels, etc. The present invention can be made into any shape, circles, squares, triangles etc., also into animal shapes or any other novelty molding available. The candy is then cooled, wrapped and packaged.

For grained types of candy, water and sugar are the basic components being mixed with other ingredients, and cooked at high temperatures (143-155° C., i.e. approximately 290-310° F.), causing the water to turn to steam. The product is transferred to a cooling wheel, where it is collected in about 68 kg (approximately 150 pound) batches, placed in a pulling machine to aerate the product, and the flavor is added.

The candy is transferred to batch rollers where it is shaped and sized. The candy then enters a former, which shapes the individual pieces. The candy is cooled at a relative humidity of 35% and enters a rotating drum where it is coated with a fine sugar. The candy is then conveyed to the graining room for four hours at approximately 32° C. (90° F.) and 60% humidity. The entrapped air and moisture causes the product to grain.

By way of example and not limitation, the following examples in Table 14 below illustrate various embodiments of the confectionery formulations of the present invention.

TABLE 14

Antimicrobial Candy Formulations
(dry weight percent basis)

| Ingredient | Example 16 | Example 17 | Example 18 | Example 19 | Example 20 |
|---|---|---|---|---|---|
| Corn Syrup | 45.00 | 43.00 | — | — | 47.00 |
| Sugar | 53.49 | 50.00 | — | — | 47.00 |
| Polyalcohols | — | — | 95.00 | 94.00 | — |
| Flavor | 1.00 | 5.00 | 3.00 | 2.00 | 2.50 |
| Color | 0.50 | 1.00 | 0.60 | 0.80 | 0.50 |
| MBE | 0.01 | 1.00 | 1.20 | 3.00 | 3.00 |
| High Intensity Sweetener | — | — | 0.20 | 0.20 | — |
| Total | 100.00 | 100.00 | 100.00 | 100.00 | 100.00 |

In accordance with the invention, each of the formulations in examples 16-20 is supplemented with a surface active agent as described above. In one exemplary embodiment, each of the examples 16-20 includes about 0.001% to about 2% surface active agent.

TABLE 15

Compressed Tablet Formulations
(dry weight percent basis)

| Ingredient | Example 21 | Example 22 | Example 23 | Example 24 | Example 25 |
|---|---|---|---|---|---|
| Sorbitol | 97.63 | 97.43 | 96.83 | 95.83 | 93.83 |
| Flavor | 1.0 | 1.0 | 1.0 | 1.0 | 1.0 |
| Magnesium Stearate | 0.97 | 0.97 | 0.97 | 0.97 | 0.97 |
| MBE | 0.01 | 0.20 | 0.50 | 1.00 | 2.00 |
| High Intensity Sweetener | 0.2 | 0.20 | 0.20 | 0.20 | 0.20 |
| SLS | 0.1 | 0.2 | 0.5 | 1.0 | 2.0 |
| Total | 100.00 | 100.00 | 100.00 | 100.00 | 100.00 |

In accordance with the invention, each of the formulations in examples 21-25 is supplemented with a surface active agent as described above. In one exemplary embodiment, each of the examples 21-25 includes about 0.001 to about 2% surface active agent.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. An oral composition for freshening the breath of consumers, the oral composition comprising
   an antimicrobial agent comprising a synergistic ratio of Magnolia Bark Extract and sodium lauryl sulfate.

2. The oral composition of claim 1 wherein the oral cavity delivery agent comprises one of a chewing gum, an edible film, a confectionary, a dentifrice, a lozenge and a mouth spray.

3. The oral composition of claim 1 wherein the sodium lauryl sulfate comprises about 0.001% to about 2% of the oral composition.

4. An oral composition for freshening the breath of consumers, the oral composition comprising:
   (a) an oral cavity delivery agent; and
   (b) an antimicrobial agent comprising a synergistic ratio of Magnolia Bark Extract and an anionic surface active agent, wherein the synergistic ratio is at least about 1 part Magnolia Bark Extract to about 1 part anionic surface active agent, wherein the anionic surface active agent comprises sodium lauryl sulfate.

5. The oral composition of claim 4 wherein the anionic surface active agent comprises about 0.001% to about 2% sodium lauryl sulfate.

6. The oral composition of claim 4 wherein the synergistic ratio of Magnolia Bark Extract to sodium lauryl sulfate is about 2 parts Magnolia Bark Extract to 1 part sodium lauryl sulfate.

7. An oral composition for freshening the breath of consumers, the oral composition comprising:
   (a) an oral cavity delivery agent; and
   (b) an antimicrobial agent comprising a synergistic ratio of Magnolia Bark Extract and surface active agent, wherein the synergistic ratio is at least about 1 part Magnolia Bark Extract to about 1 part surface active agent, wherein the surface active agent comprises sodium brasslate.

8. An oral composition for freshening the breath of consumers, the oral composition comprising;
   an antimicrobial agent comprising a synergistic ratio of Magnolia Bark Extract and sodium lauroyl sarcosinate.

9. The oral composition of claim 8 wherein the sodium lauroyl sarcosinate comprises about 0.001% to about 1.0% of the oral composition.

10. An oral composition for freshening the breath of consumers, the oral composition comprising:
   (a) an oral cavity delivery agent; and
   (b) an antimicrobial agent comprising a synergistic ratio of Magnolia Bark Extract and an anionic surface active agent, wherein the synergistic ratio is at least about 1 part Magnolia Bark Extract to about 1 part anionic surface active agent,
   wherein the anionic surface active agent comprises sodium laureth sulfate.

11. An oral composition for freshening the breath of consumers, the oral composition comprising:

an antimicrobial agent comprising a synergistic ratio of Magnolia Bark Extract and sodium laureth sulfate.

12. The oral composition of claim 11 wherein the sodium laureth sulfate comprises about 0.001% to about 2.0% of the oral composition 13. An oral composition for freshening the breath of consumers, the oral composition comprising a synergistic ratio of Magnolia Bark Extract and a surface active agent, the surface active agent comprising sodium lauryl sulfate, wherein the synergistic ratio is about 1 part to about 4 parts Magnolia Bark Extract to about 1 part surface active agent.

14. The oral composition of claim 13 wherein the surface active agent comprises about 0.001% to about 2% of the oral composition.

15. An oral composition for freshening the breath of consumers, the oral composition comprising a synergistic ratio of Magnolia Bark Extract and a surface active agent, the surface active agent comprising sodium lauroyl sarcosinate, wherein the synergistic ratio is about 1 part to about 4 parts Magnolia Bark Extract to about 1 part surface active agent.

16. The oral composition of claim 15 wherein the surface active agent comprises about 0.001% to about 2% of the oral composition.

* * * * *